United States Patent
Gayer et al.

(10) Patent No.: US 6,235,743 B1
(45) Date of Patent: May 22, 2001

(54) HALOGEN PYRIMIDINYL ARYL (THIO) ETHERS AS PESTICIDES

(75) Inventors: Herbert Gayer, Monheim; Peter Gerdes, Aachen; Ulrich Heinemann, Leichlingen; Bernd-Wieland Krüger, Bergisch Gladbach; Ralf Tiemann, Leverkusen; Stefan Dutzmann, Langenfeld; Gerd Hänssler, Leverkusen; Klaus Stenzel, Düsseldorf, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/297,666

(22) PCT Filed: Oct. 29, 1997

(86) PCT No.: PCT/EP97/05954

§ 371 Date: May 5, 1999

§ 102(e) Date: May 5, 1999

(87) PCT Pub. No.: WO98/21189

PCT Pub. Date: May 22, 1998

(30) Foreign Application Priority Data

Nov. 11, 1996 (DE) .............................................. 196 46 407

(51) Int. Cl.[7] ........................ C07D 239/56; C07D 239/52; A01N 43/54

(52) U.S. Cl. ............................................ 514/269; 544/319

(58) Field of Search .............................. 544/319; 514/269

(56) References Cited

U.S. PATENT DOCUMENTS

| | | | |
|---|---|---|---|
| 5,723,471 | 3/1998 | De Fraine | 514/274 |
| 5,773,445 | 6/1998 | Gayer et al. | 514/269 |

OTHER PUBLICATIONS

Chem. Ber. 90, (month unavailable) 1957, pp. 942–951, Bredereck et al, Formamid–Reaktionen, VIII[1] Eine Neue Pyrimidin–Synthese[2].

J. Chem. Soc. (month unavailable) 1955, pp. 3478–3480, Chesterfield et al, Pyrimidines. Part VIII. Halogeno–and Hydrazino–pyrimidines.

*Primary Examiner*—John M. Ford
(74) *Attorney, Agent, or Firm*—Joseph C. Gil

(57) ABSTRACT

The invention relates to novel halogenopyrimidines, to two processes for their preparation and to their use as pesticides.

6 Claims, No Drawings

HALOGEN PYRIMIDINYL ARYL (THIO) ETHERS AS PESTICIDES

This is a 371 of PCT/EP97/05954 filed Oct. 29, 1997.

TECHNICAL FIELD OF THE INVENTION

The invention relates to novel halogenopyrimidines, to two processes for their preparation and to their use as microbicides.

BACKGROUND OF THE INVENTION

Certain pyrimidines with a similar substitution pattern and their fungicidal action are already known (GB-A 2253624). However, the activity of these prior art compounds, in particular at low application rates and concentrations, is not entirely satisfactory in all areas of use.

DETAILED DESCRIPTION OF THE INVENTION

This invention, accordingly, provides the novel halogenopyrimidines of the general formula (I)

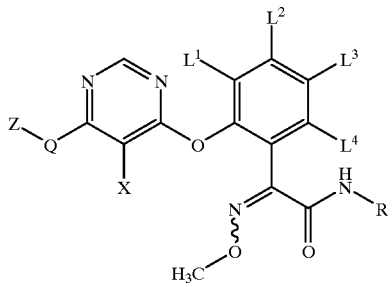

(I)

in which
Z represents respectively optionally substituted cycloalkyl, aryl or heterocyclyl,
R represents hydrogen or alkyl,
Q represents oxygen or sulphur and
X represents halogen,
$L^1$, $L^2$, $L^3$ and $L^4$ are identical or different and, independently of one another, each represents hydrogen, halogen, cyano, nitro, respectively optionally halogen-substituted alkyl, alkoxy, alkylthio, alkylsulphinyl or alkylsulphonyl.

In the definitions, the saturated or unsaturated hydrocarbon chains, such as alkyl, alkanediyl, alkenyl or alkinyl, are in each case straight-chain or branched, including in combinations with hetero atoms, such as, for example, in alkoxy, alkylthio or alkylamino.

Aryl represents aromatic mono- or polycyclic hydrocarbon rings, such as, for example, phenyl, naphthyl, anthranyl, phenanthryl, preferably phenyl or naphthyl, in particular phenyl.

Heterocyclyl represents saturated or unsaturated, and aromatic, ring-shaped compounds in which at least one ring member is a hetero atom, i.e. an atom other than carbon. If the ring contains more than one hetero atom, these may be identical or different. Preferred hetero atoms are oxygen, nitrogen or sulphur. Optionally, the ring-shaped compounds may form a polycyclic ring system together with other carbocyclic or heterocyclic fused or bridged rings. Preference is given to mono- or bicyclic ring systems, in particular to mono- or bicyclic aromatic ring systems.

Cycloalkyl represents saturated carbocyclic compounds in the form of a ring which may form a polycyclic ring system together with other carbocyclic fused or bridged rings.

Furthermore, it has been found that the novel halogenopyrimidines of the general formula (I) are obtained when a) 2-(2-hydroxy-phenyl)-2-methoxyimino-acetamides of the formula (II)

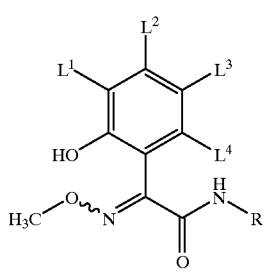

(II)

in which
R, $L^1$, $L^2$, $L^4$ and $L^4$ are each as defined above are reacted with a substituted halogenopyrimidine of the general formula (III)

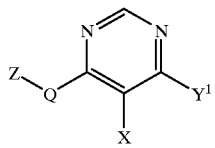

(III)

in which
Z, Q and X are each as defined above and
$Y^1$ represents halogen,
if appropriate in the presence of a diluent, if appropriate in the presence of an acid acceptor and if appropriate in the presence of a catalyst, or b) phenoxypyrimidines of the general formula (IV)

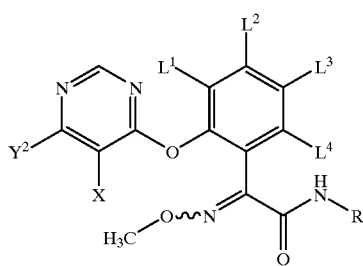

(IV)

in which
R, X, $L^1$, $L^2$, $L^3$ and $L^4$ are each as defined above and
$Y^2$ represents halogen
are reacted with a ring compound of the general formula (V)

Z—Q—H   (V)

in which
Z and Q are each as defined above,
if appropriate in the presence of a diluent, if appropriate in the presence of an acid acceptor and if appropriate in the presence of a catalyst.

Finally, it has been found that the novel halogenopyrimidines of the general formula (I) have very strong fungicidal activity.

The compounds according to the invention may be present as mixtures of various possible isomeric forms, in particular of stereoisomers such as, for example, E- and Z-isomers. Both the E- and the Z-isomers and any mixtures of these isomers are claimed.

The invention preferably provides compounds of the formula (I) in which

Z
represents cycloalkyl having 3 to 7 carbon atoms which is in each case optionally mono- to disubstituted by halogen, alkyl or hydroxyl;
represents heterocyclyl having 3 to 7 ring members which is optionally substituted by alkyl having 1 to 4 carbon atoms;
or represents phenyl or naphthyl, each of which is optionally mono- to tetrasubstituted by identical or different substituents, the possible substituents preferably being selected from the list below:
halogen, cyano, nitro, amino, hydroxyl, formyl, carboxyl, carbamoyl, thiocarbamoyl;
respectively straight-chain or branched alkyl, hydroxyalkyl, oxoalkyl, alkoxy, alkoxyalkyl, alkylthioalkyl, dialkoxyalkyl, alkylthio, alkylsulphinyl or alkylsulphonyl having in each case 1 to 8 carbon atoms;
respectively straight-chain or branched alkenyl or alkenyloxy having in each case 2 to 6 carbon atoms;
respectively straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms;
respectively straight-chain or branched halogenoalkenyl or halogenoalkenyloxy having in each case 2 to 6 carbon atoms and 1 to 11 identical or different halogen atoms;
respectively straight-chain or branched alkylamino, dialkylamino,
alkylcarbonyl, alkylcarbonyloxy, alkoxycarbonyl, alkylaminocarbonyl, dialkylaminocarbonyl, arylalkylaminocarbonyl, dialkylaminocarbonyloxy, alkenylcarbonyl or alkinylcarbonyl having 1 to 6 carbon atoms in the respective hydrocarbon chains;
cycloalkyl or cycloalkyloxy having in each case 3 to 6 carbon atoms;
alkylene having 3 or 4 carbon atoms, oxyalkylene having 2 or 3 carbon atoms or dioxyalkylene having 1 or 2 carbon atoms, each of which is doubly attached and in each case optionally mono- to tetrasubstituted by identical or different substituents from the group consisting of fluorine, chlorine, oxo, methyl, trifluoromethyl and ethyl;

or a grouping 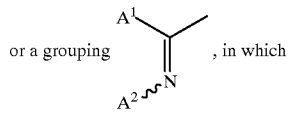, in which $A^1$ represents hydrogen, hydroxyl or alkyl having 1 to 4 carbon atoms or cycloalkyl having 1 to 6 carbon atoms and
$A^2$ represents hydroxyl, amino, methylamino, phenyl, benzyl or represents respectively optionally cyano-, hydroxyl-, alkoxy-, alkylthio-, alkylamino-, dialkylamino- or phenyl-substituted alkyl or alkoxy having 1 to 4 carbon atoms, or represents alkenyloxy or alkinyloxy having in each case 2 to 4 carbon atoms,
and phenyl, phenoxy, phenylthio, benzoyl, benzoylethenyl, cinnamoyl, heterocyclyl or phenylalkyl, phenylalkyloxy, phenylalkylthio or heterocyclyl-alkyl having in each case 1 to 3 carbon atoms in the respective alkyl moieties, each of which is optionally mono- to trisubstituted in the ring moiety by halogen and/or straight-chain or branched alkyl or alkoxy having 1 to 4 carbon atoms, R represents hydrogen or methyl, Q represents oxygen or sulphur and X represents fluorine, chlorine, bromine or iodine, $L^1$, $L^2$, $L^3$ and $L^4$ are identical or different and, independently of one another, each represents hydrogen, halogen, cyano, nitro, or represent alkyl, alkoxy, alkylthio, alkylsulphinyl or alkylsulphonyl having in each case 1 to 6 carbon atoms and being in each case optionally substituted by 1 to 5 halogen atoms.

The invention in particular provides compounds of the formula (I) in which

Z
represents cyclopentyl or cyclohexyl, each of which is optinally mono- to disubstituted by fluorine, chlorine, methyl, ethyl or hydroxyl;
represents optionally methyl- or ethyl-substituted thienyl, pyridyl or furyl;
or represents phenyl or naphthyl, each of which is optionally mono- to tetrasubstituted by identical or different substituents, the possible substituents preferably being selected from the list below:
fluorine, chlorine, bromine, iodine, cyano, nitro, amino, hydroxyl, formyl, carboxyl, carbamoyl, thiocarbamoyl,
methyl, ethyl, n- or i-propyl, n-, i-, s- or t-butyl, 1-, 2-, 3-, neo-pentyl, 1-, 2-, 3-, 4-(2-methylbutyl), 1-, 2-, 3-hexyl, 1-, 2-, 3-, 4-, 5-(2-methylpentyl), 1-, 2-, 3-(3-methylpentyl), 2-ethylbutyl, 1-, 3-, 4-(2,2-dimethylbutyl), 1-, 2-(2,3-dimethylbutyl), hydroxymethyl, hydroxyethyl, 3-oxobutyl, methoxymethyl, dimethoxymethyl,
methoxy, ethoxy, n- or i-propoxy,
methylthio, ethylthio, n- or i-propylthio, methylsulphinyl, ethylsulphinyl, methylsulphonyl or ethylsulphonyl,
vinyl, allyl, 2-methylallyl, propen-1-yl, crotonyl, propargyl, vinyloxy, allyloxy, 2-methylallyloxy, propen-1-yloxy, crotonyloxy, propargyloxy,
trifluoromethyl, trifluoroethyl,
difluoromethoxy, trifluoromethoxy, difluorochloromethoxy, trifluoroethoxy, difluoromethylthio, trifluoromethylthio, difluorochloromethylthio, trifluoromethylsulphinyl or trifluoromethylsulphonyl,
methylamino, ethylamino, n- or i-propylamino, dimethylamino, diethylamino,
acetyl, propionyl, methoxycarbonyl, ethoxycarbonyl, methylaminocarbonyl, ethylaminocarbonyl, dimethylaminocarbonyl, diethylaminocarbonyl, dimethylaminocarbonyloxy, diethylaminocarbonyloxy, benzylaminocarbonyl, acryloyl, propioloyl, cyclopentyl, cyclohexyl,
propanediyl, ethyleneoxy, each of which is doubly attached and in each case optionally mono- to tetra-substituted by identical or different substituents from the group consisting of fluorine, chlorine, oxo, methyl and trifluoromethyl, or a grouping 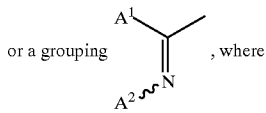, where $A^1$ represents hydrogen, methyl or hydroxyl and
$A^2$ represents hydroxyl, methoxy, ethoxy, amino, methylamino, phenyl, benzyl or hydroxyethyl, and phenyl, phenoxy, phenylthio, benzoyl, benzoylethenyl, cinnamoyl, benzyl, phenylethyl, phenylpropyl, benzyloxy, benzylthio, 5,6-dihydro-1,4,2-dioxazin-3-ylmethyl, triazolylmethyl, benzoxazol-2-ylmethyl, 1,3-dioxan-2-yl, benzimidazol-2-yl, dioxol-2-yl, oxadiazolyl, each of which is optionally mono- to trisubstituted in the ring moiety by halogen and/or straight-chain or branched alkyl or alkoxy having 1 to 4 carbon atoms, R represents hydrogen or methyl, Q represents oxygen or sulphur and X represents fluorine or chlorine and $L^1$, $L^2$, $L^3$ and $L^4$ are identical or different and, independently of one another, each represents hydrogen, fluorine, chlorine, bromine, cyano, nitro, methyl, ethyl, n- or i-propyl, n-, i-, s- or t-butyl, methoxy, ethoxy, n- or i-propoxy, methylthio, ethylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl.

In a very particularly preferred group of compounds, Z represents optionally substituted phenyl.

In a further very particularly preferred group of compounds $L^1$ and $L^3$ independently of one another each represent methyl and in particular hydrogen and $L^2$ and $L^4$ each represent hydrogen.

Particular preference is given to compounds of the formula (I) in which X represents fluorine.

The abovementioned general or preferred radical definitions apply both to the end products of the formula (I) and correspondingly to the starting materials or intermediates required in each case for the preparation.

The specific definitions given for these radicals in the respective combinations or preferred combinations of radicals can be replaced by any radical definitions of other preferred ranges, independently of the combination given in each case.

These radical definitions can be combined with one another as desired, thus including combinations between the ranges of preferred compounds indicated.

The formula (II) provides a general definition of the 2-(2-hydroxy-phenyl)-2-methoxyimino-acetamides required as starting materials for carrying out the process a) according to the invention. In this formula (II), R, $L^1$, $L^2$, $L^3$ and $L^4$ each preferably or in particular have those meanings which have already been indicated above, in connection with the description of the compounds of the formula (I) according to the invention, as preferred or particularly preferred for R, $L^1$, $L^2$, $L^3$ and $L^4$.

The starting materials of the formula (II) are known and can be prepared by known processes (cf. for example WO-A 9524396).

The formula (III) provides a general definition of the halogenopyrimidines further required as starting materials for carrying out the process a) according to the invention. In this formula (III), Z, Q and X each preferably or in particular have those meanings already indicated above, in connection with the description of the compounds of the formula (I) according to the invention, as preferred or particularly preferred for Z, Q and X. $Y^1$ represents halogen, preferably fluorine or chlorine.

The starting materials of the formula (III) are known and/or can be prepared by known methods (cf. for example DE-A 4340181; Chem. Ber., 90<1957>942, 951).

The formula (IV) provides a general definition of the phenoxypyrimidines required as starting materials for carrying out the process b) according to the invention. In this formula (IV), R, X, $L^1$, $L^2$, $L^3$ and $L^4$ each preferably or in particular have those meanings already indicated above, in connection with the description of the compounds of the formula (I) according to the invention, as preferred or particularly preferred for R, X, $L^1$, $L^2$, $L^3$ and $L^4$. $Y^2$ represents halogen, preferably fluorine or chlorine.

The starting materials of the formula (IV) are novel and also form part of the subject matter of the present application.

The phenoxypyrimidines of the general formula (IV) are obtained (process b-1) when 2-(2-hydroxy-phenyl)-2-methoxyimino-acetamides of the formula (II) are reacted with a trihalogenopyrimidine of the general formula (VI)

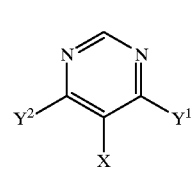

(VI)

in which

X, $Y^1$ and $Y^2$ are identical or different and each represent halogen, if appropriate in the presence of a diluent, if appropriate in the presence of an acid acceptor and if appropriate in the presence of a catalyst.

The hydroxy compounds of the formula (II) required as starting materials for carrying out the process b-1) according to the invention have already been described in connection with the description of the process a) according to the invention.

The formula (VI) provides a general definition of the trihalogenopyrimidines further required as starting materials for carrying out the process b-1) according to the invention. In this formula (VI), X, $Y^1$ and $Y^2$ each represent halogen, preferably fluorine or chlorine.

The trihalogenopyrimidines are known and/or can be prepared by known methods (cf. for example Chesterfield et al., J. Chem. Soc., 1955; 3478, 3480).

The formula (V) provides a general definition of the ring compounds further required as starting materials for carrying out the process b) according to the invention. In this formula (V), Z and Q each preferably or in particular have those meanings which have already been indicated above, in connection with the description of the compounds of the formula (I) according to the invention, as preferred or particularly preferred for Z and Q.

The ring compounds of the formula (V) are known chemicals for synthesis, or they can be prepared by simple methods.

Suitable diluents for carrying out the processes a), b) and b-1) according to the invention are all inert organic solvents. These include preferably ethers, such as diethyl ether, diisopropyl ether, methyl t-butyl ether, methyl t-amyl ether, dioxane, tetrahydrofuran, 1,2-dimethoxyethane, 1,2-diethoxyethane or anisole; nitriles, such as acetonitrile, propionitrile, n- or i-butyronitrile or benzonitrile; amides, such as N,N-dimethylformamide, N,N-dimethylacetamide, N-methylformanilide, N-methylpyrrolidone or hexamethylphosphoric triamide; sulphoxides, such as dimethyl sulphoxide; or sulphones, such as sulpholane.

If appropriate, the processes a), b) and b-1) according to the invention are carried out in the presence of a suitable acid acceptor. Suitable acid acceptors are all customary inorganic or organic bases. These include preferably alkaline earth metal or alkali metal hydrides, hydroxides, alkoxides, carbonates or bicarbonates, such as, for example, sodium hydride, sodium amide, potassium tert-butoxide, sodium hydroxide, potassium hydroxide, sodium carbonate, potassium carbonate, potassium bicarbonate or sodium bicarbonate.

Suitable catalysts for the processes a), b) and b-1) according to the invention are all copper(I) salts, such as, for example, copper(I) chloride, copper(I) bromide or copper(I) iodide.

The reaction temperatures used when carrying out the processes a), b) and b-1) according to the invention can be varied within a relatively wide range. Generally, the processes are carried out at temperatures of from −20° C. to 100° C., preferably at temperatures of from −10° C. to 80° C.

In the practice of process a) according to the invention for preparing the compounds of the formula (I), generally 0.5 to 15 mol, preferably 0.8 to 8 mol, of the substituted halogenopyrimidine of the formula (III) are employed per mole of the 2-(2-hydroxy-phenyl)-2-methoxyimino-acetamide of the formula (II).

In the practice of the process b) according to the invention for preparing the compounds of the formula (I), generally 0.5 to 15 mol, preferably 0.8 to 8 mol, of a ring compound of the general formula (V) are employed per mole of the phenoxypyrimidine of the formula (IV).

In the practice of the process b-1) according to the invention for preparing the compounds of the formula (IV), generally 1 to 15 mol, preferably 2 to 8 mol, of a trihalogenopyrimidine of the general formula (VI) are used per mole of the 2-(2-hydroxy-phenyl)-2-methoxyimino-acetamide of the formula (II).

All processes according to the invention are generally carried out under atmospheric pressure. However, it is also possible to operate under elevated or reduced pressure—in general between 0.1 bar and 10 bar.

The reaction, the work-up and the isolation of the reaction products is carried out by conventional methods (cf. also the preparation examples).

The compounds according to the invention have a potent microbicidal activity and can be employed for controlling undesirable microorganisms, such as fungi and bacteria, in crop protection and in the protection of materials.

Fungicides are employed in crop protection for controlling Plasmodiophoromycetes, Oomycetes, Chytridiomycetes, Zygomycetes, Ascomycetes, Basidiomycetes and Deuteromycetes.

Bactericides are employed in crop protection for controlling Pseudomonadaceae, Rhizobiaceae, Enterobacteriaceae, Corynebacteriaceae and Streptomycetaceae.

Some pathogens causing fungal and bacterial diseases which come under the generic names listed above are mentioned as examples, but not by way of limitation:

Xanthomonas species, such as, for example, *Xanthomonas campestris* pv. *oryzae*;
Pseudomonas species, such as, for example, *Pseudomonas syringae* pv. *lachrymans*;
Erwinia species, such as, for example, *Erwinia amylovora*;
Pythium species, such as, for example, *Pythium ultimum*;
Phytophthora species, such as, for example, *Phytophthora infestans*;
Pseudoperonospora species, such as, for example, *Pseudoperonospora humuli* or *Pseudoperonospora cubensis*;
Plasmopara species, such as, for example, *Plasmopara viticola*;
Bremia species, such as, for example, *Bremia lactucae*,
Peronospora species, such as, for example, *Peronospora pisi* or *P. brassicae*;
Erysiphe species, such as, for example, *Erysiphe graminis*;
Sphaerotheca species, such as, for example, *Sphaerotheca fuliginea*;
Podosphaera species, such as, for example, *Podosphaera leucotricha*;
Venturia species, such as, for example, *Venturia inaequalis*;
Pyrenophora species, such as, for example, *Pyrenophora teres* or *P. graminea* (conidia form: Drechslera, syn: Helminthosporium);
Cochliobolus species, such as, for example, *Cochliobolus sativus* (conidia form: Drechslera, syn: Helminthosporium);
Uromyces species, such as, for example, *Uromyces appendiculatus*;
Puccinia species, such as, for example, *Puccinia recondita*;
Sclerotinia species, such as, for example, *Sclerotinia sclerotiorum*
Tilletia species, such as, for example, *Tilletia caries*;
Ustilago species, such as, for example, *Ustilago nuda* or *Ustilago avenae*;
Pellicularia species, such as, for example, *Pellicularia sasakii*;
Pyricularia species, such as, for example, *Pyricularia oryzae*;
Fusarium species, such as, for example, *Fusarium culmorum*;
Botrytis species, such as, for example, *Botrytis cinerea*;
Septoria species, such as, for example, *Septoria nodorum*;
Leptosphaeria species, such as, for example, *Leptosphaeria nodorum*;
Cercospora species, such as, for example, *Cercospora canescens*;
Alternaria species, such as, for example, *Alternaria brassicae*; and
Pseudocercosporella species, such as, for example, *Pseudocercosporella herpotrichoides*.

The fact that the active compounds are well tolerated by plants at the concentrations required for controlling plant diseases permits the treatment of aerial parts of plants, of propagation stock and seeds, and of the soil.

The active compounds according to the invention can be employed particularly successfully for controlling cereal diseases, such as, for example, against Erysiphe species, Puccinia species, Fusarium species and Pyrenophora species, diseases in viticulture and fruit and vegetable growing, such as, for example, against Venturia, Sphaerotheca and Plasmopara species, Phytophthora species, or rice diseases, such as, for example, against Pyricularia species. Other cereal diseases, such as, for example, Septoria, Pyrenophora or Cochliobolus species, are also controlled succesfully. Furthermore, the compounds according to the invention may also be employed to increase the yield of crops.

Depending on their particular physical and/or chemical properties, the active compounds can be converted to the customary formulations, such as solutions, emulsions, suspensions, powders, foams, pastes, granules, aerosols and microencapsulations in polymeric substances and in coating compositions for seeds, and ULV cool and warm fogging formulations.

These formulations are produced in a known manner, for example by mixing the active compounds with extenders, that is, liquid solvents, liquefied gases under pressure, and/or solid carriers, optionally with the use of surfactants, that is emulsifiers and/or dispersants, and/or foam formers. In the case of the use of water as an extender, organic solvents can, for example, also be used as auxiliary solvents. Essentially, the following are suitable as liquid solvents: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide or dimethyl sulphoxide, or else water. Liquefied gaseous extenders or carriers are to be understood as meaning liquids which are gaseous at standard temperature and under atmospheric pressure, for example aerosol propellants such as halogenated hydrocarbons, or else butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as highly disperse silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. Suitable dispersants are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other additives can be mineral and vegetable oils.

It is possible to use colourants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 per cent by weight of active compound, preferably between 0.5 and 90%.

The active compounds according to the invention can be used as such or in their formulations also mixed with known fungicides, bactericides, acaricides, nematicides or insecticides in order thus, for example, to widen the spectrum of action or to prevent development of resistance. In many cases, synergistic effects are achieved, i.e. the activity of the mixture exceeds the activity of the individual components.

Examples of co-components in mixtures are the following compounds:

Fungicides:

aldimorph, ampropylfos, ampropylfos potassium, andoprim, anilazine, azaconazole, azoxystrobin, benalaxyl, benodanil, benomyl, benzamacril, benzamacril-isobutyl, bialaphos, binapacryl, biphenyl, bitertanol, blasticidin-S, bromuconazole, bupirimate, buthiobate, calcium polysulphide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram, debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon, edifenphos, epoxiconazole, etaconazole, ethirimol, etridiazole, famoxadon, fenapanil, fenarimol, fenbuconazole, fenfuram, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulfamide, flutolanil, flutriafol, folpet, fosetyl-aluminium, fosetyl-sodium, fthalide, fuberidazole, furalaxyl, furametpyr, furcarbonil, furconazole, furconazole-cis, furmecyclox, guazatine, hexachlorobenzene, hexaconazole, hymexazole, imazalil, imibenconazole, iminoctadine, iminoctadine albesilate, iminoctadine triacetate, iodocarb, ipconazole, iprobenfos (IBP), iprodione, irumamycin, isoprothiolane, isovaledione, kasugamycin, kresoxim-methyl, copper preparations, such as: copper hydroxide, copper naphthenate, copper oxychloride, copper sulphate, copper oxide, oxine-copper and Bordeaux mixture, mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin, nickel dimethyldithiocarbamate, nitrothal-isopropyl, nuarimol, ofurace, oxadixyl, oxamocarb, oxolinic acid, oxycarboxim, oxyfenthiin, paclobutrazole, pefurazoate, penconazole, pencycuron, phosdiphen, pimaricin, piperalin, polyoxin, polyoxorim, probenazole, prochloraz, procymidone, propamocarb, propanosine-sodium, propiconazole, propineb, pyrazophos, pyrifenox, pyrimethanil, pyroquilon, pyroxyfur, quinconazole, quintozene (PCNB), sulphur and sulphur preparations, tebuconazole, tecloftalam, tecnazene, tetcyclasis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichlamide, tricyclazole, tridemorph, triflumizole, triforine, triticonazole,
uniconazole,
validamycin A, vinclozolin, viniconazole,
zarilamide, zineb, ziram and also
Dagger G,
OK-8705,
OK-8801,
α-(1,1-dimethylethyl)-β-(2-phenoxyethyl)-1H-1,2,4-triazole-1-ethanol,
α-(2,4-dichlorophenyl)-β-fluoro-β-propyl-1H-1,2,4-triazole-1-ethanol,
α-(2,4-dichlorophenyl)-β-methoxy-α-methyl-1H-1,2,4-triazole-1-ethanol,
α-(5-methyl-1,3-dioxan-5-yl)-β-[[4-(trifluoromethyl)-phenyl]-methylene]-1H-1,2,4-triazole-1-ethanol,
(5RS,6RS)-6-hydroxy-2,2,7,7-tetramethyl-5-(1H-1,2,4-triazol-1-yl)-3-octanone,
(E)-α-(methoxyimino)-N-methyl-2-phenoxyphenylacetamide,
1-isopropyl {2-methyl-1-[[[1-(4-methylphenyl)-ethyl]-amino]-carbonyl]-propyl}-carbamate,
1-(2,4-dichlorophenyl)-2-(1H-1,2,4-triazol-1-yl)ethanone-O-(phenylmethyl)-oxime,
1-(2-methyl-1-naphthalenyl)-1H-pyrrol-2,5-dione,
1-(3,5-dichlorophenyl)-3-(2-propenyl)-2,5-pyrrolidindione,
1-[(diiodomethyl)-sulphonyl]-4-methyl-benzene,
1-[[2-(2,4-dichlorophenyl)-1,3-dioxolan-2-yl]-methyl]-1H-imidazole,
1-[[2-(4-chlorophenyl)-3-phenyloxiranyl]-methyl]-1H-1,2,4-triazole,
1-[1-[2-[(2,4-dichlorophenyl)-methoxy]-phenyl]-ethenyl]-1H-imidazole,
1-methyl-5-nonyl-2-(phenylmethyl)-3-pyrrolidinole,
2',6'-dibromo-2-methyl-4'-trifluoromethoxy-4'-trifluoro-methyl-1,3-thiazole-5-carboxanilide,
2,2-dichloro-N-[1-(4-chlorophenyl)-ethyl]-1-ethyl-3-methyl-cyclopropanecarboxamide,
2,6-dichloro-5-(methylthio)-4-pyrimidinyl-thiocyanate,
2,6-dichloro-N-(4-trifluoromethylbenzyl)-benzamide,
2,6-dichloro-N-[[4-(trifluoromethyl)-phenyl]-methyl]-benzamide,
2-(2,3,3-triiodo-2-propenyl)-2H-tetrazole,
2-[(1-methylethyl)sulphonyl]-5-(trichloromethyl)-1,3,4-thiadiazole,
2-[[6-deoxy-4-O-(4-O-methyl-β-D-glycopyranosyl)-α-D-glucopyranosyl]-amino]-4-methoxy-1H-pyrrolo[2,3-d]pyrimidine-5-carbonitrile,
2-aminobutane,
2-bromo-2-(bromomethyl)-pentanedinitrile,
2-chloro-N-(2,3-dihydro-1,1,3-trimethyl-1H-inden-4-yl)-3-pyridinecarboxamide,
2-chloro-N-(2,6-dimethylphenyl)-N-(isothiocyanatomethyl)-acetamide,
2-phenylphenol (OPP),
3,4-dichloro-1-[4-(difluoromethoxy)-phenyl]-1H-pyrrol-2,5-dione,
3,5-dichloro-N-[cyano-[(1-methyl-2-propynyl)-oxy]-methyl]-benzamide,
3-(1,1-dimethylpropyl-1-oxo-1H-indene-2-carbonitrile,
3-[2-(4-chlorophenyl)-5-ethoxy-3-isoxazolidinyl]-pyridine,
4-chloro-2-cyano-N,N-dimethyl-5-(4-methylphenyl)-1H-imidazole-1-sulphonamide,
4-methyl-tetrazolo[1,5-a]quinazolin-5(4H)-one,
8-(1,1-dimethylethyl)-N-ethyl-N-propyl-1,4-dioxaspiro[4.5]decane-2-methanamine,
8-hydroxyquinoline sulphate,
9H-xanthene-2-[(phenylamino)-carbonyl]-9-carboxylic hydrazide,
bis-(1-methylethyl)-3-methyl-4-[(3-methylbenzoyl)oxy]-2,5-thiophenedicarboxylate,
cis-1-(4-chlorophenyl)-2-(1H-1,2,4-triazol-1-yl)-cycloheptanol,
cis-4-[3-[4-(1,1-dimethylpropyl)-phenyl-2-methylpropyl]-2,6-dimethyl-morpholine hydrochloride,
ethyl [(4-chlorophenyl)-azo]-cyanoacetate,
potassium bicarbonate,
methanetetrathiol, methane sodium salt,
methyl 1-(2,3-dihydro-2,2-dimethyl-1H-inden-1-yl)-1H-imidazole-5-carboxylate,
methyl N-(2,6-dimethylphenyl)-N-(5-isoxazolylcarbonyl)-DL-alaninate,
methyl N-(chloroacetyl)-N-(2,6-dimethylphenyl)-DL-alaninate,
N-(2,3-dichloro4-hydroxyphenyl)-1-methyl-cyclohexanecarboxamide,
N-(2,6-dimethylphenyl)-2-methoxy-N-(tetrahydro-2-oxo-3-furanyl)-acetamide,
N-(2,6-dimethylphenyl)-2-methoxy-N-(tetrahydro-2-oxo-3-thienyl)-acetamide,
N-(2-chloro-4-nitrophenyl)-4-methyl-3-nitro-benzenesulphonamide,
N-(4-cyclohexylphenyl)-1,4,5,6-tetrahydro-2-pyrimidinamine,
N-(4-hexylphenyl)-1,4,5,6-tetrahydro-2-pyrimidinamine,
N-(5-chloro-2-methylphenyl)-2-methoxy-N-(2-oxo-3-oxazolidinyl)-acetamide,
N-(6-methoxy)-3-pyridinyl)-cyclopropanecarboxamide,
N-[2,2,2-trichloro-1-[(chloroacetyl)-amino]-ethyl]-benzamide,
N-[3-chloro-4,5-bis(2-propinyloxy)-phenyl]-N'-methoxy-methanimidamide,
N-formyl-N-hydroxy-DL-alanine-mono-sodium salt,
O,O-diethyl [2-(dipropylamino)-2-oxoethyl]-ethylphosphoramidothioate,
O-methyl S-phenyl phenylpropylphosphoramidothioate,
S-methyl 1,2,3-benzothiadiazole-7-carbothioate,
spiro[2H]-1-benzopyrane-2,1'(3'H)-isobenzofuran]-3'-one, Bactericides
bromopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.
Insecticides/Acaricides/Nematicides
abamectin, acephate, acrinathrin, alanycarb, aldicarb, alphamethrin, amitraz, avermectin, AZ 60541, azadirachtin, azinphos A, azinphos M, azocyclotin, *Bacillus thuringiensis,* 4-bromo-2-(4-chlorophenyl)-1-(ethoxymethyl)-5-(trifluoromethyl)-1H-pyrrole-3-carbonitrile, bendiocarb, benfuracarb, bensultap, betacyfluthrin, bifenthrin, BPMC, brofenprox, bromophos A, bufencarb, buprofezin, butocarboxin, butylpyridaben,
cadusafos, carbaryl, carbofuran, carbophenothion, carbosulfan, cartap, chloethocarb, chlorethoxyfos, chlorfenapyr, chlorfenvinphos, chlorfluazuron, chlormephos, N-[(6-chloro-3-pyridinyl)-methyl]-N'-cyano-N-methyl-ethanirnidamide, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine, deltamethrin, demeton M, demeton S, demeton S-methyl, diafenthiuron, diazinon, dichlofenthion, dichlorvos, dicliphos, dicrotophos, diethion, diflubenzuron, dimethoate, dimethylvinphos, dioxathion, disulfoton, edifenphos, emamectin, esfenvalerate, ethiofencarb, ethion, ethofenprox, ethoprophos, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, fluazuron, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivermectin, lambda-cyhalothrin, lufenuron, malathion, mecarbam, mervinphos, mesulfenphos, metaldehyde, methacrifos, methamidophos, methidathion, methiocarb, methomyl, metolcarb, milbemectin, monocrotophos, moxidectin, naled, NC 184, nitenpyram, omethoate, oxamyl, oxydemethon M, oxydeprofos, parathion A, parathion M, permethrin, phenthoate, phorate, phosalone, phosmet, phosphamidon, phoxim, pirimicarb, pirimiphos M, pirimiphos A, profenofos, promecarb, propaphos, propoxur, prothiofos, prothoate, pymetrozin, pyrachlophos, pyridaphenthion, pyresmethrin, pyrethrum, pyridaben, pyrimidifen, pyriproxifen, quinalphos, salithion, sebufos, silafluofen, sulfotep, sulprofos, tebufenozide, tebufenpyrad, tebupirimphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb, vamidothion, XMC, xylylcarb, zetamethrin.

It is also possible to admix other known active compounds, such as herbicides, fertilizers and growth regulators.

The active compounds can be used as such or in the form of their commercial formulations or the use forms prepared therefrom, such as ready-to-use solutions, suspensions, wettable powders, pastes, soluble powders, dusts and granules. They are used in the customary manner, for example by pouring, spraying, atomizing, broadcasting, foaming, brushing-on and the like. It is further possible to apply the active compounds by the ultra-low volume method or to inject the preparation of active compound, or the active compound itself, into the soil. The seeds of the plants can also be treated.

In the treatment of parts of plants, the active compound concentrations in the use forms can be varied within a substantial range. They are, in general, between 1 and 0.0001% by weight, preferably between 0.5 and 0.001% by weight.

In the treatment of seed, amounts of active compound of from 0.001 to 50 g, preferably 0.01 to 10 g, are generally required per kilogram of seed.

In the treatment of the soil, active compound concentrations of from 0.00001 to 0.1% by weight, preferably from 0.0001 to 0.02% by weight, are required at the site of action.

PREPARATION EXAMPLES

Example 1

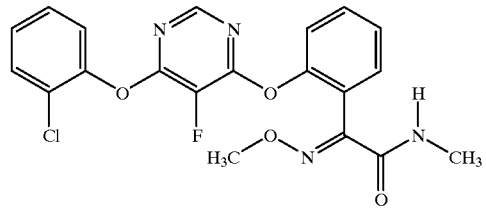

Process a)

With cooling, 0.4 g (0.01 mol) of sodium hydride (60%) are added to a mixture of 2 g (0.0096 mol) of 2-(2-hydroxyphenyl)-2-methoxyimino-N-methyl-acetamide and 2.3 g (0.0095 mol) of 4-(2-chlorophenoxy)-5,6-difluoropyrimidine in 10 ml of dimethylformamide, and the mixture is stirred at 25° C. for 12 hours. The reaction mixture is poured onto water and extracted with dichloromethane, the organic phase is dried over sodium sulphate and the solvent is distilled off under reduced pressure. The residue is chromatographed over silica gel using a mixture of identical volumina of ethyl acetate and cyclohexane. 2.1 g (48.3% of theory) of 2-{2-[6-(2-chlorophenoxy)-5-fluoro-pyrimidine-4-yloxy]-phenyl}-2-methoxyimino-N-methylacetamide are obtained.

$^1$H NMR spectrum (CDCl$_3$/TMS): δ=6 2.88/2.90 (3H); 3.82 (3H); 6.68 (1H); 7.25–7.54 (8H); 8.05 (1H) ppm.

Example 2

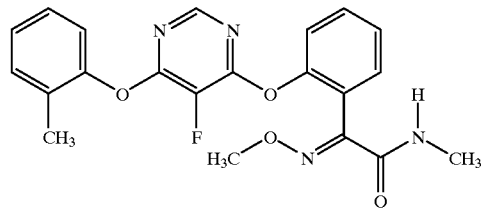

Process b)

With cooling, 0.25 g (0.0062 mol) of sodium hydride (60%) are added to a mixture of 2 g (0.0062 mol) of 2-[2-(5,6-difluoropyrimidin-4-yloxy)-phenyl]-2-methoxyimino-N-methyl-acetamide and 0.67 g (0.0062 mol) of 2-methylphenol in 20 ml of dimethylformamide, and the mixture is stirred at 25° C. for 12 hours. The reaction mixture is poured onto water and extracted with ethyl acetate, the organic phase is dried over sodium sulphate and the solvent is distilled off under reduced pressure. 1.5 g (58.9%) of 2-[2-(5-fluoro-6-o-tolyloxy-pyrimidin-4-yloxy)-phenyl]-2-methoxyimino-N-methyl-acetamide are obtained.

$^1$H NMR spectrum (CDCl$_3$/TMS): δ=6 2.21 (3H); 2.89/2.90 (3H); 3.84 (3H); 6.7 (1H,b); 7.06–7.53 (8H); 8.06 (1H) ppm.

By the methods of Examples 1 to 2, and according to the procedures in the general description of the process, the compounds of the formula (Ia) listed in Table 1 below are obtained.

TABLE 1

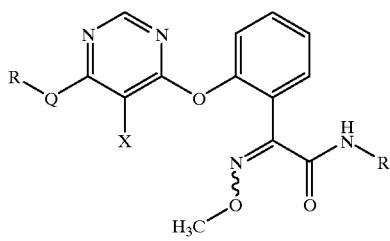

(Ia)

| Ex. No. | R | Q | X | R | M. p. (° C.) | NMR * | logP ** |
|---|---|---|---|---|---|---|---|
| 3 | phenyl | O | F | —CH₃ | 107 | 3.85 | 2.77 |
| 4 | 2-cyanophenyl | O | F | —CH₃ | 128–130 | 3.85 | 2.6 |
| 5 | 2-methoxyphenyl | O | F | —CH₃ | | 3.83 | 2.72 |
| 2 | 2-methylphenyl | O | F | —CH₃ | | 3.84 | 3.04 |
| 6 | 4-chlorophenyl | O | F | —CH₃ | | 3.85 | 3.22 |
| 7 | 2-acetylphenyl | O | F | —CH₃ | | 3.85 | 2.51 |
| 8 | 2-allyloxyphenyl | O | F | —CH₃ | | 3.82 | 3.11 |
| 9 | 2-propionyloxyphenyl | O | F | —CH₃ | | 3.85 | 2.83 |
| 10 | 2-chlorophenyl | O | F | —H | | 3.87 | 2.79 |
| 11 | 2-bromophenyl | O | F | —CH₃ | | 3.83 | 3.08 |
| 12 | 2-fluorophenyl | O | F | —CH₃ | | 3.82 | 2.85 |
| 13 | 2,4-dibromophenyl | O | F | —CH₃ | | 3.83 | 3.76 |
| 14 | 2,3-dichlorophenyl | O | F | —CH₃ | | 3.83 | 3.45 |
| 15 | 2,4-dichlorophenyl | O | F | —CH₃ | | 3.83 | 3.61 |
| 16 | 2,5-dichlorophenyl | O | F | —CH₃ | | 3.83 | 3.53 |
| 17 | 2,6-dichlorophenyl | O | F | —CH₃ | | 3.79 | 3.35 |
| 18 | 2,3-dimethylphenyl | O | F | —CH₃ | | 3.77 | 3.30 |
| 19 | 2,4-dimethylphenyl | O | F | —CH₃ | | 3.84 | 3.39 |
| 20 | 2,5-dimethylphenyl | O | F | —CH₃ | | 3.76 | 3.52 |
| 21 | 2,6-dimethylphenyl | O | F | —CH₃ | | 3.82 | 3.29 |
| 22 | 2-chloro-4-methylphenyl | O | F | —CH₃ | | 3.82 | 3.41 |
| 23 | 2-chloro-5-methylphenyl | O | F | —CH₃ | | 3.82 | 3.37 |
| 24 | 3-chloro-2-methylphenyl | O | F | —CH₃ | | 3.84 | 3.50 |
| 25 | 4-chloro-2-methylphenyl | O | F | —CH₃ | | | |
| 26 | 2-bromo-4-chlorophenyl | O | F | —CH₃ | | 3.83 | 3.65 |
| 27 | 4-bromo-2-chlorophenyl | O | F | —CH₃ | | 3.82 | 3.70 |
| 28 | phenyl | S | F | —CH₃ | | 3.81 | 3.07 |

* The ¹H NMR spectra were recorded in deuterochloroform (CDCl₃) or hexadeuterodimethyl sulphoxide (DMSO-d₆) using tetramethylsilane (TMS) as internal standard. The chemical shift is reported as δ value in ppm.
** The logP values were determined according to the EEC Directive 79/831 Annex V. A8 using HPLC (gradient method, acetonitrile/0.1% aqueous phosphoric acid)

Preparation of the Starting Materials of the Formula (II)

Example (II-1)

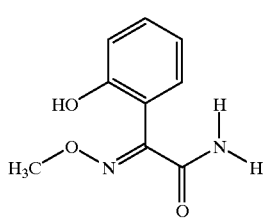

5 g (0.028 mol) of benzofuran-2,3-dione 3-(O-methyl-oxime) (WO-A 9524396) in 100 ml of tetrahydrofuran are stirred with 20 ml of 25% strength aqueous ammonia solution at 20° C. for 2 hours. The solvent is then distilled off under reduced pressure, the residue is poured onto water and extracted with ethyl acetate, the organic is dried over sodium sulphate and the solvent is distilled off under reduced pressure. The residue is recrystallized from ethanol, affording 2 g (36.4% of theory) of 2-(2-hydroxy-phenyl)-2-methoxyimino-acetamide.

log P=0.83.

GC/MS silylated:

Retention index=1827

M=341, 323, 307, 291, 149, 133, 192, 176, 135, 116, 89, 73, 45, 26.

Preparation of the Starting Materials of the Formula (III)

Example (III-1)

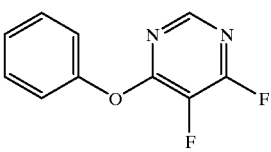

At 0° C., a solution of 42.4 g (0.45 mol) of phenol and 50.4 g (0.45 mol) of potassium tert-butoxide in 400 ml of tetrahydrofuran is added dropwise to a solution of 80 g (0.6 mol) of 4,5,6-trifluoropyrimidine in 1 l of tetrahydrofuran. After the addition, the reaction mixture is stirred at 0° C. for 30 minutes and then poured onto water and extracted with ethyl acetate. The organic phase is dried over sodium sulphate and concentrated under reduced pressure and the residue is stirred with low-boiling petroleum ether. 63.8 g (68.1% of theory) of 4-phenoxy-5,6-difluoropyrimidine of melting point 65–66° C. are obtained.

Preparation of the Starting Materials of the Formula (IV)

Example (IV-1)

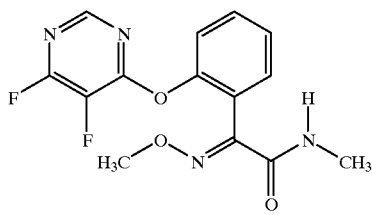

5 g (0.024 mol) of 2-(2-hydroxy-phenyl)-2-methoxyimino-N-methyl-acetamide are dissolved in 30 ml of tetrahydrofuran and cooled to 0° C. With stirring, 2.7 g (0.024 mol) of potassium tert-butoxide is added a little at a time. At 0° C., the resulting solution is added dropwise to a solution of 4,5,6-trifluoropyrimidine in 40 ml of tetrahydrofuran. The mixture is then stirred at 20° C. for 1 hour. The solvent is subsequently distilled off under reduced pressure, the residue is poured onto water and extracted with ethyl acetate, the organic phase is dried over sodium sulphate and the solvent is distilled off under reduced pressure. The mixture is stirred with diethyl ether and 3.2 g (41.3% of theory) of crystalline 2-[2-(5,6-difluoro-pyrimidin-4-yloxy)-phenyl]-2-methoxyimino-N-methyl-acetamide are filtered off.

$^1$H NMR spectrum (CDCl$_3$/TMS): δ=2.87/2.88 (3H); 3.81 (3H); 6.67 (1H, b); 7.33–7.55 (4H); 8.19/8.20 (1H) ppm.

Preparation of a Precursor of the Formula (VI)

Example (VI-1)

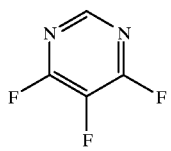

To dry a mixture of 609 g of potassium fluoride in 2.3 l of sulpholane, 500 ml of liquid are distilled off at 145° C. and 20 mbar. 1054 g of 5-chloro-4,6-difluoropyrimidine (DE-A 383558) and 25 g of tetraphenylphosphonium bromide are then added, a nitrogen pressure of 5 bar is applied and the mixture is stirred at 240° C. for 24 hours, during which the pressure increases to 11 bar. The reaction mixture is cooled to 80° C. and the pressure is released. At atmospheric pressure, the mixture is then once again slowly heated and the product is distilled off. When the temperature of the bottom has reached 200° C., the pressure is reduced to 150 mbar to speed up the distillation and to obtain more product. A total of 664 g (70.7% of theory) of 4,5,6-trifluoropyrimidine of boiling point 86 to 87° C. is obtained.

Use Examples

Example A

Plasmopara Test (Vines)/Protective

Solvent: 47 parts by weight of acetone
Emulsifier: 3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous suspension of spores of *Plasmopara viticola* and then remain in an incubation chamber at 20° C. and 100% relative atmospheric humidity for 1 day. The plants are subsequently placed in a greenhouse at 21° C. and about 90% atmospheric humidity for 5 days. The plants are then moistened and placed in an incubation chamber for 1 day.

Evaluation is carried out 6 days after the inoculation. 0% means an efficacy corresponding to that of the control, whereas an efficacy of 100% means that no infestation is observed.

In this test, for example, the following compounds of the Preparation Examples (1), (2), (3), (12), (13), (14), (15), (16), (17), (18), (20), (22), (23), (24), (26), (27), and (28) exhibit, at an exemplary active compound application rate of 100 g/ha, an efficacy of 94% or more in comparison with the untreated control.

Example B

Sphaerotheca Test (Cucumber)/Protective

Solvent: 47 parts by weight of acetone
Emulsifier: 3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous suspension of spores of *Sphaerotheca fuliginea*. The plants are subsequently placed in a greenhouse at about 23° C. and a relative humidity of about 70%.

Evaluation is carried out 10 days after the inoculation. 0% means an efficacy corresponding to that of the control, whereas an efficacy of 100% means that no infestation is observed.

In this test, for example, the following compounds of the Preparation Examples (1), (2), (3), (6), (7), (9), (12), (13), (14), (15), (17), (18), (20), (21), (22), (23), (24), (26), (27) and (28) exhibit, at an exemplary active compound application rate of 100 g/ha, an efficacy of 91% or more in comparison with the untreated control.

Example C

Venturia Test (Apple)/Protective

Solvent: 47 parts by weight of acetone
Emulsifier: 3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous suspension of conidia of the causative organism of apple scab (*Venturia inaequalis*) and then remain in an incubation chamber at about 20° C. and 100% relative humidity for 1 day.

The plants are then placed in a greenhouse at about 21° C. and a relative atmospheric humidity of about 90%.

Evaluation is carried out 12 days after the inoculation. 0% means an efficacy corresponding to that of the control, whereas 100% means that no infestation is observed.

In this test, for example, the following compounds of the Preparation Examples (2), (3), (4), (5), (6), (8), (9), (12), (14), (17), (18), (21) and (28) exhibit, at an exemplary active compound application rate of 10 g/ha, an efficacy of 96% or more in comparison with the untreated control.

Example D
Erysiphe test (Barley)/Protective

| | |
|---|---|
| Solvent: | 10 parts by weight of N-methyl-pyrrolidone |
| Emulsifier: | 0.6 part by weight of alkylaryl polyglycol ether |

To produce a suitable preparation. of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate.

After the spray coating has dried on, the plants are dusted with spores of *Erysiphe graminis* f.sp. *hordei*.

The plants are placed in a greenhouse at a temperature of about 20° C. and a relative humidity of about 80%, in order to promote the development of mildew pustules.

Evaluation is carried out 7 days after the inoculation. 0% means an efficacy corresponding to that of the control, whereas an efficacy of 100% means that no infestation is observed.

In this test, for example, the following compounds of the Preparation Examples (2), (3), and (8) exhibit, at an exemplary active compound application rate of 250 g/ha, an efficacy of 100% in comparison with the untreated control.

Example E
Erysiphe Test (Barley)/Curative

| | |
|---|---|
| Solvent: | 10 parts by weight of N-methyl-pyrrolidone |
| Emulsifier: | 0.6 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for curative activity, young plants are dusted with spores of *Erysiphe graminis* f.sp. *hordei*. 24 hours after the inoculation, the plants are sprayed with the preparation of active compound at the stated application rate.

The plants are placed in a greenhouse at a temperature of about 20° C. and a relative humidity of about 80%, in order to promote the development of mildew pustules.

Evaluation is carried out 7 days after the inoculation. 0% means an efficacy corresponding to that of the control, whereas an efficacy of 100% means that no infestation is observed.

In this test, the compounds according to the invention mentioned in Examples (2), (3), (6), (9) and (18) exhibit, at an application rate of 250 g/ha, an efficacy of 90% or more.

Example F
Pyricularia Test (Rice)/protective

| | |
|---|---|
| Solvent: | 12.5 parts by weight of acetone |
| Emulsifier: | 0.3 part by weight of alkylaryl polyglycol ether |

To produce a suitable preparation of active compound, 1 part by weight of active compound is mixed with the stated amount of solvent, and the concentrate is diluted with water and the stated amount of emulsifier to the desired concentration.

To test for protective activity, young rice plants are sprayed with the preparation of active compound to run-off point. One day after the spray coating has dried on, the plants are inoculated with an aqueous suspension of spores of *Pyricularia oryzae*. The plants are subsequently placed in a greenhouse at a relative humidity of 100% and 25° C.

Evaluation is carried out 4 days after the inoculation.

0% means an efficacy corresponding to that of the control, whereas an efficacy of 100% means that no infestation is observed.

In this test, for example, the following compounds of the Preparation Examples (1), (2), (3), (4), (8), (9), (10), (20), (21), (22) and (24) exhibit, at an exemplary active compound application rate of 750 g/ha, an efficacy of 80% in comparison with the untreated control.

Example G
Puccinia Test (Wheat)/protective

| | |
|---|---|
| Solvent: | 25 parts by weight of N,N-dimethylacetamide |
| Emulsifier: | 0.6 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are sprayed with a suspension of conidia of *Puccinia recondita*. The plants remain in an incubation chamber at 20° C. and 100% relative humidity for 48 hours.

The plants are then placed in a greenhouse at a temperature of about 20° C. and a relative atmospheric humidity of 80%, in order to promote the development of rust pustules.

Evaluation is carried out 10 days after the inoculation. 0% means an efficacy that corresponds to that of the control, whereas an efficacy of 100% means that no infestation is observed.

In this test, the compounds according to the invention mentioned in Examples (1), (2), (5), (12), (13), (14), (15), (16), (24), and (26) exhibit, at an application rate of 250 g/ha, an efficacy of 90% of more.

Example H
*Fusarium nivale* (var. *nivale*) Test (Wheat)/protective

| | |
|---|---|
| Solvent: | 25 parts by weight of N,N-dimethylacetamide |
| Emulsifier: | 0.6 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are sprayed with a suspension of conidia of *Fusarium nivale* (var. nivale).

The plants are placed in a greenhouse under transparent incubation cages at a temperature of about 15° C. and a relative atmospheric humidity of about 100%.

Evaluation is carried out 4 days after the inoculation. 0% means an efficacy that corresponds to that of the control, whereas an efficacy of 100% means that no infestation is observed.

In this test, the compounds according to the invention mentioned in Examples (1), (2), (13), (14), (15), (16), (17), (20), (21), (22), (24) and (26) exhibit, at an application rate of 250 g/ha, an efficacy of 90% or more.

Example I
*Pyrenophora teres* Test (Barley)/protective

| Solvent: | 25 parts by weight of N,N-diemethylacetamide |
| Emulsifier: | 0.6 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are sprayed with a suspension of conidia of *Pyrenophora teres*. The plants remain in an incubation chamber at 20° C. and 100% relative atmospheric humidity for 48 hours.

The plants are then placed in a greenhouse at a temperature of about 20° C. and a relative atmospheric humidity of about 80%.

Evaluation is carried out 7 days after the inoculation. 0% means an efficacy that corresponds to that of the control, whereas an efficacy of 100% means that no infestation is observed.

In this test, the compounds according to the invention mentioned in Examples (17) and (28) exhibit, at an application rate of [lacuna] g/ha, an efficacy of 90% or more.

Example K
Phytophthora Test (Tomato)/protective

| Solvent: | 47 parts by weight of acetone |
| Emulsifier: | 3 parts by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous suspension of spores of *Phytophthora infestans*. The plants are then placed in an incubation chamber at about 20° C. and 100% relative atmospheric humidity.

Evaluation is carried out 3 days after the inoculation. 0% means an efficacy that corresponds to that of the control, whereas an efficacy of 100% mans that no infestation is observed.

In this test, the compounds according to the invention mentioned in examples (8), (9) and (10) exhibit, at an application rate of [lacuna] g/ha, an efficacy of 96% or more.

What is claimed is:
1. A compound of the formula (I)

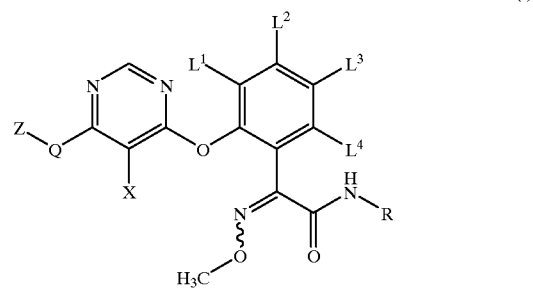

wherein
Z represents a moiety selected from the group consisting of cycloalkyl having 3 to 7 carbon atoms which is in each case unsubstituted or mono- to disubstituted by halogen, alkyl or hydroxyl; thienyl, pyridyl or furyl, which in each case is unsubstituted or substituted by alkyl having 1 to 4 carbon atoms; and phenyl or naphthyl, each of which is unsubstituted or mono- to tetrasubstituted by identical or different substituents, the substituents selected from the group consisting of:
halogen, cyano, nitro, amino, hydroxyl, formyl, carboxyl, carbamoyl, thiocarbamoyl; straight-chain and branched alkyl, hydroxyalkyl, oxoalkyl, alkoxy, alkoxyalkyl, alkylthioalkyl, dialkoxyalkyl, alkylthio, alkylsulphinyl and alkylsulphonyl having in each case 1 to 8 carbon atoms;
straight-chain and branched alkenyl and alkenyloxy having in each case 2 to 6 carbon atoms; straight-chain and branched halogenoalkyl, halogenoalkoxy, halogenoalkylthio, halogenoalkylsulphinyl and halogenoalkylsulphonyl having in each case 1 to 6 carbon atoms and 1 to 13 identical or different halogen atoms;
straight-chain and branched halogenoalkenyl and halogenoalkenyloxy having in each case 2 to 6 carbon atoms and 1 to 11 identical or different halogen atoms;
straight-chain and branched alkylamino, dialkylamino, alkylcarbonyl, alkylcarbonyloxy, alkoxycarbonyl, alkylaminocarbonyl, dialkylaminocarbonyl, arylalkylaminocarbonyl, dialkylaminocarbonyloxy, alkenylcarbonyl and alkynylcarbonyl having 1 to 6 carbon atoms in the hydrocarbon chains; cycloalkyl and cycloalkyloxy having in each case 3 to 6 carbon atoms;
alkylene having 3 or 4 carbon atoms, oxyalkylene having 2 or 3 carbon atoms and dioxyalkylene having 1 or 2 carbon atoms, each of which is attached doubly and in each case which is unsubstituted or mono- to tetrasubstituted by identical or different substituents from the group consisting of fluorine, chlorine, oxo, methyl, trifluoromethyl and ethyl; and a grouping

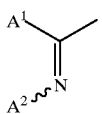

wherein
A¹ represents hydrogen, hydroxyl or alkyl having 1 to 4 carbon atoms and
A² represents hydroxyl, amino, methylamino, benzyl; unsubstituted or cyano-, hydroxyl-, alkoxy-, alkylthio-, alkylamino-, dialkylamino- or phenyl-substituted alkyl or alkoxy having 1 to 4 carbon atoms; alkenyloxy or alkynyloxy having in each case 2 to 4 carbon atoms; phenyl, phenoxy, phenylthio, benzoyl, benzoylethenyl, cinnamoyl, phenylalkyl, phenylalkyloxy, phenylalkylthio, 5,6-dihydro-1,4,2-dioxazin-3-ylmethyl, triazolylmethyl, benzoxazol-2-ylmethyl, 1,3-dioxan-2-yl, benzimidazol-2-yl, dioxol-2-yl and oxadiazolyl, having in each case 1 to 3 carbon atoms in the alkyl moiety and each of which is unsubstituted or mono- to trisubstituted in the ring moiety by a substituent selected from the group consisting of halogen and straight-chain and branched alkyl and alkoxy having 1 to 4 carbon atoms,
R represents hydrogen or methyl,
Q represents oxygen or sulphur and
X represents fluorine, chlorine, bromine or iodine,
L¹, L², L³ and L⁴ are identical or different and, independently of one another, each represents hydrogen, halogen, cyano, nitro, or represent alkyl, alkoxy, alkylthio, alkylsulphinyl or alkylsulphonyl having in each case 1 to 6 carbon atoms and being in each case unsubstituted or substituted by 1 to 5 halogen atoms.

2. The compound of claim 1 wherein
Z represents a moiety selected from the group consisting of cyclopentyl or cyclohexyl, each of which is unsubstituted or mono- to disubstituted by fluorine, chlorine, methyl, ethyl or hydroxyl; unsubstituted or methyl- or ethyl-substituted thienyl, pyridyl or furyl; phenyl or naphthyl, each of which is unsubstituted or mono- to tetrasubstituted by identical or different substituents, the substituent selected from the group consisting of fluorine, chlorine, bromine, iodine, cyano, nitro, amino, hydroxyl, formyl, carboxyl, carbamoyl, thiocarbamoyl; methyl, ethyl, n- and i-propyl, n-, i-, s- and t-butyl, 1-, 2-, 3-, neo-pentyl, 1-, 2-, 3-, 4-(2-methylbutyl), 1-, 2-, 3-hexyl, 1-, 2-, 3-, 4-, 5-(2-methylpentyl), 1-, 2-, 3-(3-methylpentyl), 2-ethylbutyl, 1-, 3-, 4-(2,2-dimethylbutyl), 1-, 2-(2,3-dimethylbutyl); hydroxymethyl, hydroxyethyl; 3-oxobutyl, methoxymethyl, dimethoxymethyl, methoxy, ethoxy, n- and i-propoxy; methylthio, ethylthio, n- and i-propylthio; methylsulphinyl, ethylsulphinyl, methylsulphonyl and ethylsulphonyl; vinyl, allyl, 2-methylallyl, propen-1-yl, crotonyl, propargyl; vinyloxy, allyloxy, 2-methylallyloxy, propen-1-yloxy, crotonyloxy, propargyloxy; trifluoromethyl, trifluoroethyl, difluoromethoxy, trifluoromethoxy, difluorochloromethoxy, trifluoroethoxy, difluoromethylthio, trifluoromethylthio, difluorochloromethylthio, trifluoromethylsulphinyl or trifluoromethylsulphonyl; methylamino, ethylamino, n- and i-propylamino, dimethylamino, diethylamino; acetyl, propionyl, methoxycarbonyl, ethoxycarbonyl, methylaminocarbonyl, ethylaminocarbonyl, dimethylaminocarbonyl, diethylaminocarbonyl, dimethylaminocarbonyloxy, diethylaminocarbonyloxy, benzylaminocarbonyl, acryloyl, propioloyl, cyclopentyl, cyclohexyl; propanediyl, ethyleneoxy, each of which is doubly attached and in each case unsubstituted or mono- to tetrasubstituted by identical or different substituents from the group consisting of fluorine, chlorine, oxo, methyl and trifluoromethyl; and a grouping

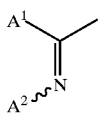

wherein
A¹ represents hydrogen, methyl or hydroxyl and
A² represents hydroxyl, methoxy, ethoxy, amino, methylamino, benzyl or hydroxyethyl; or phenyl, phenoxy, phenylthio, benzoyl, benzoylethenyl, cinnamoyl, benzyl, phenylethyl, phenylpropyl, benzyloxy, benzylthio, 5,6-dihydro-1,4,2-dioxazin-3-ylmethyl, triazolylmethyl, benzoxazol-2-ylmethyl, 1,3-dioxan-2-yl, benzimidazol-2-yl, dioxol-2-yl, oxadiazolyl, each of which is unsubstituted or mono- to trisubstituted in the ring moiety by a substituent selected from the group consisting of halogen and straight-chain or branched alkyl or alkoxy having 1 to 4 carbon atoms,
R represents hydrogen or methyl,
Q represents oxygen or sulphur and
X represents fluorine or chlorine and
L¹, L², L³ and L⁴ are identical or different and, independently of one another, each represents hydrogen, fluorine, chlorine, bromine, cyano, nitro, methyl, ethyl, n- or i-propyl, n-, i-, s- or t-butyl, methoxy, ethoxy, n- or i-propoxy, methylthio, ethylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy difluoromethylthio, difluorochloromethylthio, trifluoromethylthio, trifluoromethylsulphinyl or trifluoromethylsulphonyl.

3. A compound of the formula (I) according to claim 1 wherein Q represents oxygen.

4. A compound of the formula

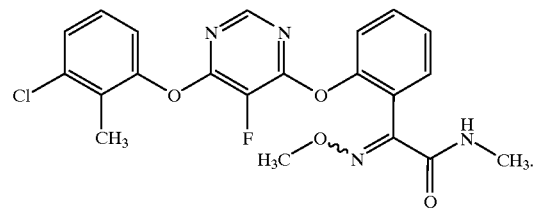

5. A microbiocidal composition comprising a microbicidally effective amount of a compound according to claim 1 and an inert diluent.

6. A method of combating undesired microorganisms comprising the step of applying a microbicidally active amount of a compound according to claim 1 to such microorganisms and/or to their habitat.

* * * * *